(12) United States Patent
Moore et al.

(10) Patent No.: US 6,238,912 B1
(45) Date of Patent: May 29, 2001

(54) METHOD AND APPARATUS FOR CONTACTING GAS AND LIQUID

(76) Inventors: Philip Coley Moore, Lammas Farm Upper Benefield, Oundle Cambrideshire PE8 5AN (GB); Stephen Robert Mercer Ellis, 49 Garth Avenue, Surby Isle of Man IM9 6QU (GB)

( * ) Notice: Subject to any disclaimer, the term of this patent is extended or adjusted under 35 U.S.C. 154(b) by 0 days.

(21) Appl. No.: 08/981,828

(22) PCT Filed: Jul. 15, 1996

(86) PCT No.: PCT/GB96/01683

§ 371 Date: Mar. 16, 1998

§ 102(e) Date: Mar. 16, 1998

(87) PCT Pub. No.: WO97/03927

PCT Pub. Date: Feb. 6, 1997

(30) Foreign Application Priority Data

Jul. 15, 1995 (GB) .................................... 9514541

(51) Int. Cl.$^7$ ........................................... C12M 1/00
(52) U.S. Cl. .................... 435/289.1; 435/286.6; 435/293.2; 422/176; 261/79.2
(58) Field of Search .................. 261/79.2, 150, 261/157; 435/286.6, 286.7, 289.1, 293.2; 422/176, 189, 224

(56) References Cited

U.S. PATENT DOCUMENTS 4,834,343 * 5/1989 Boyes ................................. 261/79.2

FOREIGN PATENT DOCUMENTS 2 070 967 * 9/1981 (GB) .

* cited by examiner

*Primary Examiner*—David A. Redding
(74) *Attorney, Agent, or Firm*—Oblon, Spivak, McClelland, Maier & Neustadt, P.C.

(57) ABSTRACT

A method and apparatus for contacting a gas and liquid. An elongated cylindrical reactor has an inlet region of reduced cross-sectional area at a first end. At least some of the gas or liquid is introduced into the inlet region in a direction tangential to the longitudinal axis of the reactor by way of an inlet to cause rotational flow within the inlet region. The gas or liquid flows into the remainder of the reactor at such a velocity as to cause more intimate mixing of the liquid and gas. Additional gas or liquid can be introduced through a second inlet disposed in an intermediate region of the reactor so that the fluid introduced flows in a generally longitudinal direction or rotational direction.

47 Claims, 13 Drawing Sheets

FIG. 13

Calculation of KLa

- $C^*$ = equilibrium concentration of oxygen in water
- $C_i$ = concentration of oxygen in water at reactor inlet
- $C_f$ = concentration of oxygen in water at reactor output
- $F_c$ = flowrate of downward liquid flow
- $F_{st}$ = swirl flowrate at reactor top
- $F_{sb}$ = swirl flowrate at reactor bottom
- $H_d$ = height of bubble dispersion
- $E_g$ = gas holdup
- $Q$ = total liquid flow coming into and leaving reactor
- $V_r$ = volume of reactor
- $KLa$ (pf) = gas-liquid mass transfer coefficient calculated using classical str model
- $KLa$ (str) = gas-liquid mass transfer coefficient calculated using classical str model

| Run No. | Temp C | P (psig) | H atm | C* ppm | Ci ppm | Cf ppm | Fc 1/min | Fst 1/min | Fsb 1/min | Hd cm | Eg | Q/Vr | Kla (pf) | Kla (str) |
|---|---|---|---|---|---|---|---|---|---|---|---|---|---|---|
| ag | 10.8 | 15 | 33054.51 | 54.64072 | 6.97 | 23.4 | 18 | | | 100 | 0.5 | 0.296004 | 0.12509 | 0.155673 |
| ah | 10.8 | 15 | 33054.51 | 54.64072 | 6.97 | 37.3 | 18 | | | 100 | 0.5 | 0.296004 | 0.299337 | 0.517729 |
| ai | 10.8 | 19 | 33054.51 | 69.21158 | 6.97 | 43.6 | 20 | | | 100 | 0.5 | 0.328893 | 0.29205 | 0.470387 |
| aj | 10.8 | 20 | 33054.51 | 72.85429 | 6.97 | 52.5 | 18 | | | 100 | 0.5 | 0.296004 | 0.347689 | 0.662124 |
| ak | 11.8 | 18 | 33797.09 | 64.12822 | 7.41 | 55.1 | 6.5 | 10 | 0 | 100 | 0.5 | 0.271337 | 0.498647 | 1.433291 |
| al | 11.4 | 20 | 33499.92 | 71.88564 | 7.41 | 59.3 | 9 | 10 | 0 | 100 | 0.5 | 0.312449 | 0.510457 | 1.288211 |
| am | 11.4 | 20 | 33499.92 | 71.88564 | 7.41 | 60.4 | 8 | 10 | 2 | 100 | 0.5 | 0.328893 | 0.567403 | 1.517377 |
| an | 11.4 | 23 | 33499.92 | 82.66849 | 7.41 | 66 | 8 | 10 | 3.5 | 100 | 0.5 | 0.35356 | 0.53296 | 1.24277 |
| ao | 11.4 | 24 | 33499.92 | 86.26277 | 7.41 | 68 | 8 | 9 | 4 | 100 | 0.5 | 0.345338 | 0.505132 | 1.14572 |
| ap | 11.7 | 16 | 33722.78 | 57.12846 | 7.05 | 40.6 | 10 | 10 | 0 | 114 | 0.4 | 0.240419 | 0.266506 | 0.48801 |
| aq | 11.7 | 17 | 33722.78 | 60.69899 | 7.05 | 48.6 | 10 | 10 | 0 | 114 | 0.4 | 0.240419 | 0.358066 | 0.82564 |
| ar | 11.7 | 20 | 33722.78 | 71.41058 | 7.05 | 56.4 | 10 | 10 | 0 | 114 | 0.4 | 0.240419 | 0.349989 | 0.790421 |
| as | 11.7 | 20 | 33722.78 | 71.41058 | 7.05 | 53 | 9.5 | 10 | 2 | 107 | 0.4 | 0.275358 | 0.344632 | 0.687253 |
| at | 12.2 | 22 | 34094.4 | 77.69544 | 7.05 | 53.8 | 9.5 | 10 | 3 | 100 | 0.4 | 0.308337 | 0.334233 | 0.603244 |
| au | 12 | 24 | 33945.73 | 85.12988 | 7.05 | 55.2 | 9.5 | 10 | 4 | 97 | 0.45 | 0.362183 | 0.347289 | 0.582666 |

Runs aq – aj : classical CDC
Runs ak – ao : Using bottom swirl and wide insert
Runs ap – au : Using bottom swirl and medium size insert

Calculation of KLa

C* = equilibrium concentration of oxygen in water
Ci = concentration of oxygen in water at reactor inlet
Cf = concentration of oxygen in water at reactor output
Fc = flowrate of downward liquid flow
Fst = swirl flowrate at reactor top
Fsb = swirl flowrate at reactor bottom Hd = height of bubble dispersion
Eg = gas holdup
Q = total liquid flow coming into and leaving reactor
Vr = volume of reactor
kLa (pf) = gas-liquid mass transfer coefficient calculated using classical str model
kLa (str) = gas-liquid mass transfer coefficient calculated using classical str model

| P (psig) | H atm | C* ppm | Ci ppm | Cf ppm | Fc 1/min | Fst 1/min | Fsb 1/min | Hd cm | Eg | Q/Vr | Kla (pf) | Kla (str) |
|---|---|---|---|---|---|---|---|---|---|---|---|---|
| 13 | 33425.66 | 46.82948 | 7.15 | 25.6 | 6.8 | 9 | | 25.9 | 0.5 | 1.003188 | 0.627437 | 0.871845 |
| 13 | 33425.66 | 46.82948 | 7.15 | 30.8 | 5 | 9 | | 65.6 | 0.5 | 0.350953 | 0.318106 | 0.517799 |
| 13 | 33277.16 | 47.03845 | 7.15 | 29.8 | 6.8 | 7 | | 89.5 | 0.5 | 0.25356 | 0.212723 | 0.333159 |
| 13 | 33277.16 | 47.03845 | 7.15 | 25.4 | 6.8 | 9 | | 60.2 | 0.5 | 0.431604 | 0.263976 | 0.364018 |
| 13 | 33277.16 | 47.03845 | 7.15 | 37.8 | 8.6 | 9 | | 100 | 0.5 | 0.259826 | 0.38005 | 0.862012 |
| 16 | 33202.93 | 58.02291 | 7.15 | 40.7 | 6.5 | 9 | | 100 | 0.5 | 0.254892 | 0.274596 | 0.493661 |
| 16 | 33277.16 | 57.89348 | 7.15 | 43.9 | 5 | 9 | | 100 | 0.5 | 0.230225 | 0.296574 | 0.604623 |
| 16 | 33351.4 | 57.76461 | 7.15 | 50.6 | 3.5 | 9.75 | | 100 | 0.5 | 0.217892 | 0.432166 | 1.365616 |
| 13 | 33351.4 | 46.93374 | 7.15 | 41.2 | 7 | 9 | | 100 | 0.5 | 0.263115 | 0.509677 | 1.582514 |
| 13 | 33351.4 | 46.93374 | 7.15 | 39.3 | 3 | 10 | | 100 | 0.5 | 0.213781 | 0.352926 | 0.900351 |
| 16 | 33227.16 | 57.89348 | 7.15 | 38.5 | 5 | 9 | | 100 | 0.5 | 0.230225 | 0.221441 | 0.372162 |
| 16 | 33351.4 | 57.76461 | 7.26 | 49.4 | 3 | 10 | | 100 | 0.5 | 0.213781 | 0.384389 | 1.077004 |
| 14 | 33351.4 | 50.54403 | 7.26 | 40.7 | 3 | 10.5 | | 100 | 0.5 | 0.222003 | 0.328768 | 0.75414 |
| 14 | 33351.4 | 50.54403 | 7.26 | 43.8 | 4 | 10.5 | | 100 | 0.5 | 0.238448 | 0.443304 | 1.291939 |
| 14 | 33351.4 | 50.54403 | 7.26 | 45.2 | 5 | 10.5 | | 100 | 0.5 | 0.254892 | 0.533185 | 1.80961 |
| 14 | 33351.4 | 50.54403 | 7.26 | 46 | 7 | 10.5 | | 100 | 0.5 | 0.287782 | 0.648651 | 2.453473 |
| 20 | 33351.4 | 72.20576 | 7.26 | 56.3 | 5 | 10.5 | | 100 | 0.5 | 0.254892 | 0.358601 | 0.785874 |
| 20 | 33351.4 | 72.20576 | 7.26 | 62.3 | 4 | 10.5 | | 100 | 0.5 | 0.238448 | 0.448386 | 1.324902 |
| 20 | 33351.4 | 72.20576 | 7.26 | 65.4 | 3 | 10.5 | | 100 | 0.5 | 0.222003 | 0.500791 | 1.896519 |

FIG. 14

METHOD AND APPARATUS FOR CONTACTING GAS AND LIQUID

BACKGROUND OF THE INVENTION

1. Field of the Invention

The present invention relates to a method and apparatus for contacting gas and liquid. More particularly, but not exclusively, it relates to a method of and apparatus for initiating and at least partially effecting a fermentation or bioreaction process in which a gas such as oxygen or an oxygen containing gas, is introduced into a liquid, which may contain a solid phase therein. The reactor into which the gas and liquid are fed may contain a micro-organism. aerobic in the case of the gas being oxygen, which causes a reaction of the solid or liquid phase.

As stated above, the gas used is preferably oxygen or an oxygen containing gas, such as air. However, the invention is not limited to use of air or oxygen, and other gases may be used within the scope of the present invention. Similarly, the liquids involved are usually aqueous, but other liquids, which term includes mixtures of liquids or emulsions or dispersions, also fall within the scope of the present invention. In this connection, the term liquid will be used herein for convenience to refer to such liquids and to liquids containing solids in the form of suspensions or solutions.

2. Discussion of the Background

It is known to carry out such bioreactions in a stirred vessel, wherein air is introduced by means of sparge pipes into a tank containing liquid (as defined above as including possibly solid phases). After a period of time, the chosen micro-organism will have effected sufficient reaction for clear or treated liquid to be run off, possibly after a settling stage. One disadvantage with this process is the length of time taken to effect the reaction, which may be as long as 24 hours, and of course the amount of space needed to accommodate the volume of liquid/solids to be treated. It would be advantageous if a similar reaction could be accomplished within a shorter time and also using an apparatus which occupies a smaller volume. Indeed, it would also be advantageous to effect an improved gas/liquid contact in a short time, possibly as little as 20 seconds, and then allow a bioreaction to take place at a slower rate in a second or subsequent reactor. The improved gas/liquid contact and possible recirculation may enable overall treatment times to be reduced considerably, say from 24 hours to 2 hours.

So-called waterfall columns are known in which a jet of liquid is introduced into a gas filled space, entraining some of the gas to form a shallow froth above the liquid in the reactor.

It is known from British Patent No 1596738 to mix gas and liquids more effectively by introducing them co-currently in a downward flowing reactor. Such mixing however, can still create a gas space above the froth, although it can produce gas bubbles of such a size that the interfacial area between gas and liquid is increased, and therefore the contacting process is improved. Use of such apparatus, however, produces a zone of froth at an uppermost part of the reactor column wherein gas/liquid contact and mass transfer is not at its most effective.

It is also known from U.S. Pat. No. 4,834,343 to increase further the contact between gas and liquid by introducing at least part of the flow in a direction tangential to the longitudinal axis of the reactor. However this process has been carried out only in reactor columns having a "swirl" zone of substantially constant diameter and volume. This "swirl" zone is formed by the mixture in that zone of a vertically downward fluid stream at the top of the column, with a tangential inlet below it. This has been found to be unsatisfactory.

SUMMARY OF THE INVENTION

It is an object of the present invention to provide a method and apparatus which can further improve the contact between gas and liquid (as defined above optionally to include a solid phase) and enable a bioreaction to be carried out in and subsequent to the reactor.

According to a first aspect of the invention, there is provided a method of contacting a gas and a liquid which comprises providing an elongate substantially cylindrical reactor having adjacent a first end thereof an inlet region of reduced cross sectional area, introducing at least some of the gas and/or the liquid into said inlet region in a direction tangential to the longitudinal axis of the reactor to cause rotational flow of the gas/liquid mixture within said inlet region and therefrom into the remainder of the reactor and at such a velocity as to cause more intimate mixing of the liquid and gas within the confines of said inlet region.

The velocity should be such that the flow re-disperses any large bubbles of gas that might accumulate at the top of the column. Also the exit downflow velocity from around the diameter of the insert, which being greater than the downflow velocity below the insert, reduces the tendency for larger bubbles to rise to the top of the column.

The high inlet velocity introduction of the gas/liquid mixture into a relatively confined area promotes mixing of the gas and liquid and minimises gas separation from the mixture.

The gas and liquid may be combined initially at or upstream of a Venturi constriction or orifice plate which is itself at or upstream of the reactor inlet region.

The constriction or orifice may preferably be located at the point of tangential entry, and thereby serve to disperse the gas and produce only small bubbles.

In this case the velocity of flow of the gas/liquid at the constriction may optionally be greater than 150 cms/sec.

The method may further include introducing a liquid and/or gas stream through a second inlet disposed at an intermediate region of said reactor which may be so arranged that said gas and/or liquid introduced therethrough flows in a direction either generally longitudinally of the reactor, or in a rotational direction.

In this case, the second inlet may be disposed at a point where the rotational flow in the reactor causes a central vortex region to form.

In one embodiment of the method, the first inlet may be provided for liquid, as defined herein, which is recirculated from a second reactor fed from the outlet of this first reactor, and the second inlet may be provided for fresh liquid, optionally including gas, to be treated.

Alternatively, or additionally, the fresh material may be introduced through said second inlet at a comparatively slow rate.

The second inlet for liquid and/or gas to the reactor may comprise a pipe extending into the intermediate region of the reactor and adapted to cause rotational movement of material inlet thereby in either a co-current or countercurrent sense with respect to the direction of rotational movement of the gas/liquid/solid content thereof induced as a result of the initial tangential inflow.

The pipe comprising the second inlet may extend longitudinally into the reactor.

Alternatively the pipe comprising the second inlet may extend transversely into the reactor.

The method may include heating the gas and/or liquid introduced through the first or second inlet so as to raise the overall temperature of the liquid within the reactor.

Additionally or alternatively, the method may comprise introducing additional liquids and/or gas by means of a third inlet for liquid which may be provided at an intermediate region of said reactor.

Said third inlet may be so disposed that the liquid introduced therethrough is directed tangentially to the longitudinal axis of the reactor.

In this case the liquid so introduced may be so directed as to be co-current with the previously generated rotational flow.

Alternatively, the liquid so introduced may be so directed as to be counter-current to the previously generated rotational flow.

According to a second aspect of the present invention, there is provided an apparatus for contacting gas and/or liquid, comprising an elongate reactor, inlet means adjacent a first end thereof and outlet means therefrom adjacent a second end thereof, the inlet means comprising an inlet for gas and/or liquid disposed to direct the incoming gas and liquid tangentially to the longitudinal axis of the reactor and into an inlet zone thereof which has a smaller cross sectional area than that of the major part of the reactor, whereby the incoming gas and/or liquid has a higher initial rotational velocity.

The inlet zone may comprise an annulus adjacent the first end of the reactor, said annulus preferably having an outer diameter substantially equal to that of the reactor, and an inner diameter formed by a substantially cylindrical, conical, frustoconical insert or an insert which is a combination of any thereof.

The inlet zone may have a cross sectional area which increases either progressively or step wise as it extends from the inlet means.

The insert may have a surface provided with protrusions or corrugations to promote increased turbulence.

A second inlet may be provided to deliver liquid and/or gas to a point radially adjacent to or upstream of a longitudinally downstream portion of the insert.

Such secondary gas/liquid introduction may minimise any vortex which could be caused by the rotational flow of the originally introduced liquid/gas mixture, or may add to or maintain the rate of rotational flow.

The second inlet may comprise a pipe extending transversely into the reactor from a side wall thereof.

Alternatively, it may comprise a pipe extending longitudinally into the reactor and passing through the insert.

One further alternative would be to provide an inlet to the interior of the insert, which in this case would be provided with an aperture at a downstream end to allow the fluid introduced to pass into the reactor.

The aperture may be at the base of the insert, or at an intermediate point.

The aperture may alternatively comprise a pipe extending from and longitudinally beyond the insert, or beyond a radially larger portion thereof.

In all these cases, the second inlet may be adapted to introduce fluid co-current to the existing rotational flow, and thereby maintain or supplement it, or countercurrent to the existing rotational flow.

The insert may have a cylindrical, conical or frustoconical shape, or a combination of the two.

The second inlet may be disposed adjacent a lower portion of the insert.

The insert may have a corrugated or roughened surface.

The inlet zone may alternatively comprise a zone of diameter less then the general diameter of the reactor downstream thereof.

An additional pipe may be provided yet further downstream adapted to introduce further gas/liquid mixture to a median zone of the reactor.

The third pipe may be so configured as to introduce the liquid in a tangential direction to cause rotational flow of the introduced liquid.

The flow may be either co-current or counter-current to the rotational flow generated by the initial introduction of gas/liquid mixture.

According to a third aspect of the present invention, there is provided an apparatus for carrying out a bioreaction involving a gas and a liquid, as hereinbefore defined, the apparatus comprising a first reactor vessel having an inlet zone at one end thereof of reduced cross sectional area compared to the general diameter of the first reactor, inlet means into said inlet zone to introduce the gas/liquid mixture in a tangential direction to the longitudinal axis of the reactor, and outlet means at an opposite end of the reactor, a second reactor having an inlet means connected to the outlet means of said first reactor, stirring means therein and outlet means therefrom.

Liquid from said second reactor may be recirculated to an inlet of said first reactor.

Liquid from the second reactor may be fed to the primary inlet of the first reactor, or it may be fed thereto at one or more subsidiary inlets to said first reactor.

Means to introduce additional gas to any such recirculated feed may be provided.

According to a fourth aspect of the present invention, there is provided an apparatus for treating sewage sludge or other organic waste utilising an apparatus described according to the second or third aspects of the invention.

According to a fifth aspect of the present invention, there is provided a method of treating sewage sludge or other organic waste, according to the method described above in the first aspect of the present invention.

BRIEF DESCRIPTION OF THE DRAWINGS

Embodiments of the present invention will now be more particularly described by way of example and with reference to the accompanying drawings, in which:

FIG. 13 illustrates an example according to the present invention; and

FIG. 14 illustrates an additional example according to the present invention.

BEST MODES FOR CARRYING OUT THE INVENTION

Figure 1A:
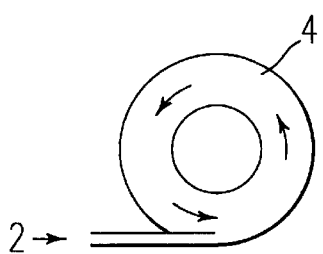
FIG. 1A is a cross sectional view thereof downwardly.
Figure 1:
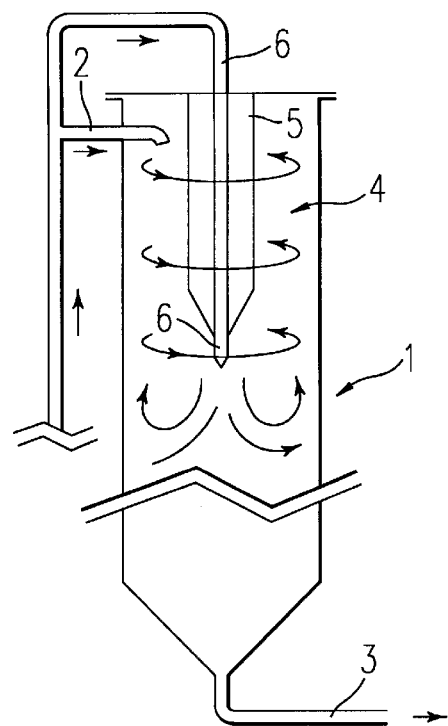
FIG. 1 shows schematically a reactor embodying the present invention.
Figure 9:
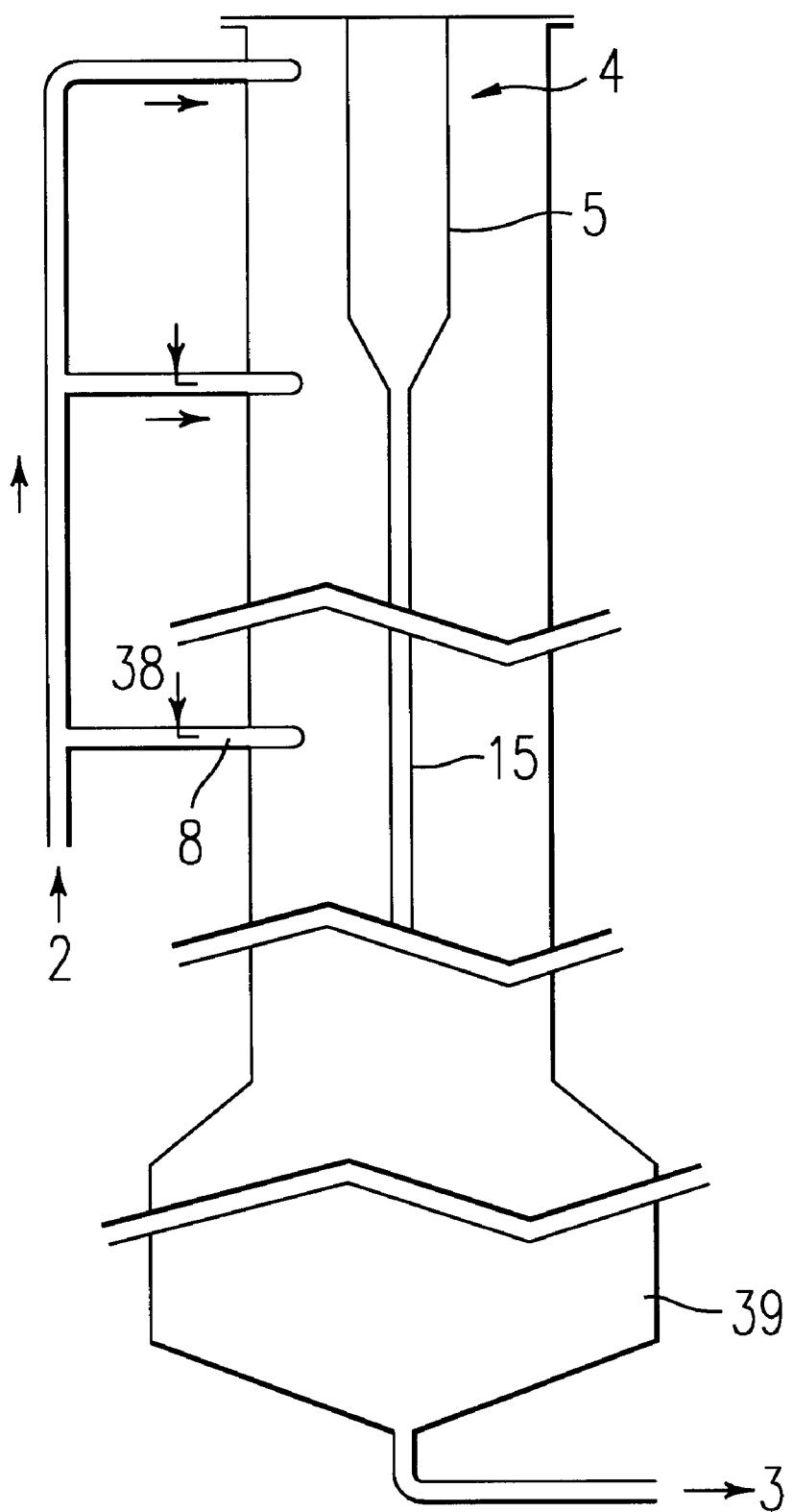
FIG. 9 shows a further embodiment in which liquid only is injected into an upper part of the column and gas/liquid mixtures are inserted at lower points thereof, which points have a reaction zone of greater volume than at the primary input.

Referring now to the drawings, there is shown in FIG. 1 an elongate reactor 1, having an inlet 2 and an outlet 3 disposed adjacent opposite ends of the reactor 1. The reactor 1 is of substantially uniform diameter, but at an inlet zone 4, adjacent to the inlet 2, there is provided a concentric inner insert 5 to form an inner wall defining with the reactor wall an annular inlet zone 4. The insert 5 may have a cylindrical shape, a conical shape, a frustoconical shape or, as shown in FIG. 1, a combination of the two. Other shapes are of course possible, including such a shape as shown in FIG. 9 and which comprises, in downward direction, a cylinder, a frustocone of maximum diameter equal to that of the cylinder, and an elongate extension 15 beyond the downward facing apex of the frustocone. The extension 15 may occupy between 5 and 30% of the cross sectional area of the reactor. This extension 15 will help to avoid the formation of a vortex and will increase the mixing and turbulence, whether or not the secondary inlet, at the centre of the column introduces fluid in a co-current or countercurrent direction. However, such an extension may not be necessary given preferred fluid flow patterns.

The liquid, as defined above possibly to include a solids constituent, to be treated is mixed with oxygen either in pure form, or as air, and passes via inlet 2 into the annular inlet zone 4. The mixture may pass through a Venturi constriction or an orifice plate to improve pick-up of the gas by the liquid to be treated. The velocity of the liquid/gas mixture at the Venturi or orifice plate is preferably greater than 150 cms/sec. The actual velocity of the fluid mixture upon entering the reactor will depend on the distance between the Venturi or orifice and the reactor. The inlet pipe 2 is so arranged that the resulting stream of liquid/gas mixture enters the reactor 1 in a direction tangential to the longitudinal axis of the reactor 1. The tangential inflow may be seen more clearly from FIG. 1A.

The introduction of the gas/liquid mixture at a relatively high velocity into the comparatively restricted space of the annular inlet zone 4 ensures that gas/liquid mixing is continued and maximized, and that the upper part of the reactor thereby contains a stable froth. As more liquid/gas is introduced, the froth moves downwardly at a rate which may be in the region of 10 cms/sec, or greater. As the intimate mixture of gas and liquid moves downwardly, it enters the larger diameter zone of the reactor but still has a large rotational component of velocity, the flow being in a generally helically downward direction.

Rotational circulation flow of fluid in the column caused by tangential introduction can lead to the formation of a vortex in the center of the reactor column immediately below the insert 5. When an extension 15 is present, this effect is minimized by the presence the insert extension 15, the cross sectional area of which is less than the area of the insert adjacent the first inlet. Adjacent this extension 15, there may be provided a second inlet 6 to introduce additional liquid or liquid and gas.

Figure 2:
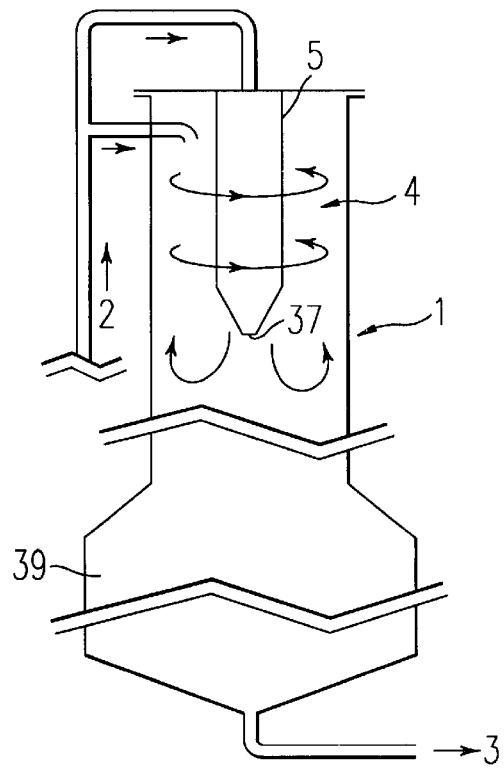
FIG. 2 shows schematically a second embodiment of reactor having an enlarged base reaction zone volume.

A secondary inlet 6 may be introduced from the side of the reactor 1 or it may be introduced longitudinally through pipe 6. In FIG. 1, pipe 6 passes through the insert 5 into the "vortex" region of the reactor. In FIG. 2, the secondary input is made directly to the interior of the insert 5, and passes via a downward facing aperture 37 directly into such region. The effect of such downward longitudinal flow is essentially the same as would be achieved by the inlet pipe 6.

However, co-current introduction of introduced fluid, or introduction from or introduction of the fluid longitudinally from the top of the reactor will have a tendency to reduce further such a vortex and will increase rotational velocity and will thereby give less large bubble formation. Counter current introduction of fluid at this second inlet is more likely to fill the vortex, and will cause more turbulence which may be desirable in some circumstances. The reduction in the overall rotation caused by countercurrent inlet flow can be compensated for by providing a stirrer having a relatively slow rotation rate. Indeed, such a stirrer may have advantages in dispersing solids, when they are present in any one or more of the inlet flows.

The amount of liquid introduced by such secondary inlet 6 may be between 5 and 30% by volume of the total liquid introduced, although greater or lesser amounts may be added at this stage. Preferably, but not necessarily, the liquid material introduced through said secondary pipe 6 is identical to that introduced through the primary inlet 2, and may be similarly oxygenated or gasified.

Figure 3:
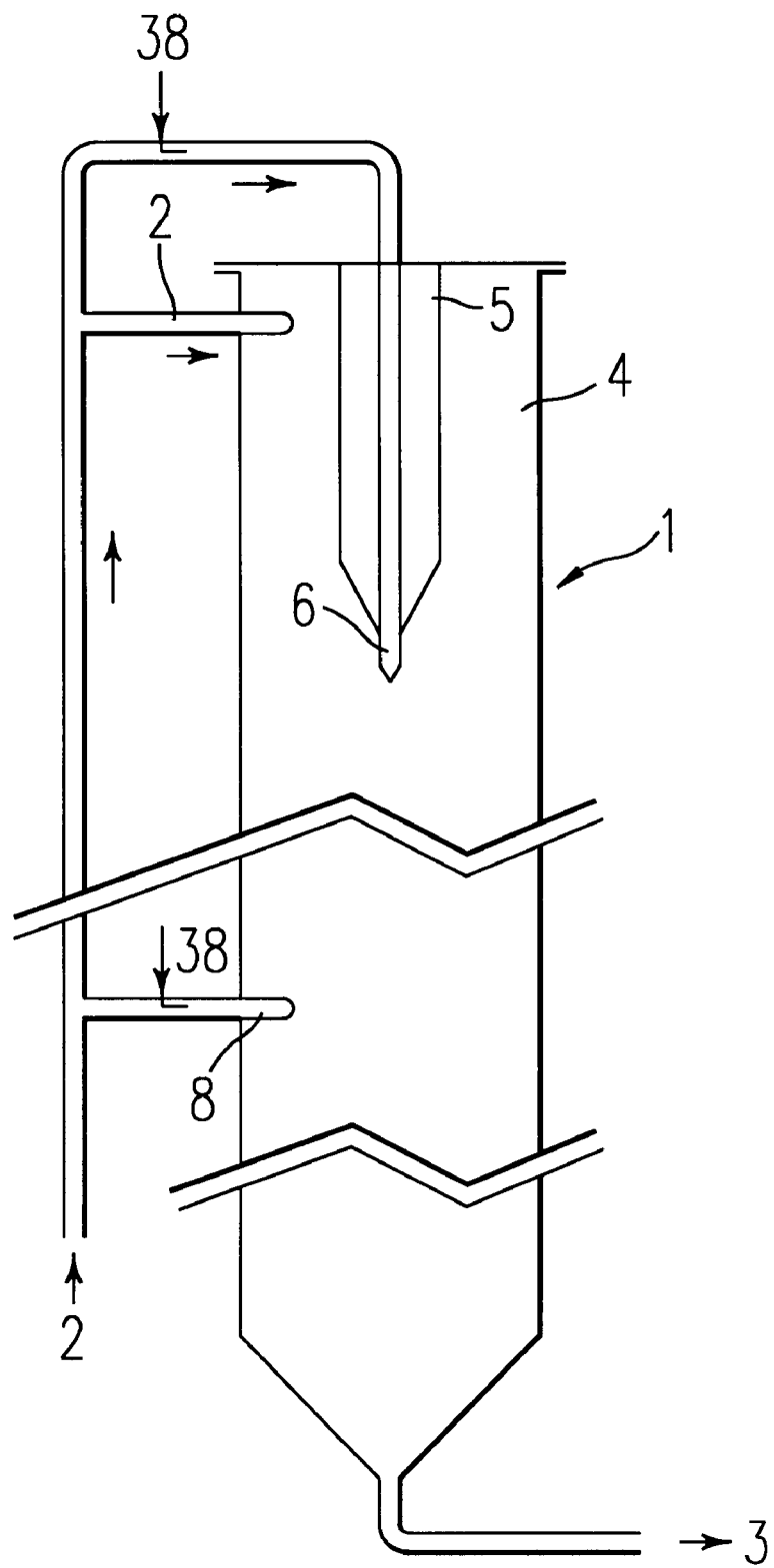
FIG. 3 shows schematically another embodiment of reactor including a third inlet.

Referring now to FIG. 3, there is shown an alternative to FIG. 2 in which the secondary inlet 6 is directed downwardly through the insert 5. However, the purpose of this is similar to that of the embodiment shown in FIG. 2. The liquid and/or gas introduced at this point may be heated to heat overall the liquid in the reactor and thereby optimize the reaction conditions therein. As a further development of this principle, a hollow insert 5 may include a space into which the secondary inlet 6 debouches and, in the case where this inlet is heated, there will be heat transfer to the gas/liquid mixture introduced via inlet 2 during its most violent mixing phase. The liquid introduced through inlet 6 may then exit into the reactor via an aperture 37 in the base of the insert 5.

Referring now to FIG. 3, there is shown a tertiary inlet 8 which may serve to introduce liquid or liquid/gas mixture at a point further downstream in the reactor. The tertiary inlet 8 comprises a pipe extending to a point adjacent to the longitudinal axis of the reactor 1, and so is configured as to release the liquid therefrom in a tangential direction so as to cause a rotational flow thereof within the liquid passing down from the primary inlet 2 and the secondary inlet 6. Depending on the needs of the process being carried out in the reactor, the tertiary inlet 8 may be so disposed as to introduce the liquid in a direction which is co-current or counter-current to the rotational flow of the liquid already present in the reactor. The purpose of this tertiary inlet 8 is to increase contact between gas and liquid at a point in the lower level of froth formation. The liquid introduced may be water or the liquid to be treated or a mixture of the liquid/gas or liquid to be treated. An alternative embodiment shown in FIG. 7 has both secondary and tertiary flows in a longitudinal direction.

In any of the embodiments of the invention, it will be possible to introduce only liquid (as hereinbefore defined) through pipe 2 in a tangential direction into the reduced volume inlet space 4. Gas, such as oxygen, may then be introduced, optionally admixed with a liquid, which may be a liquid to be treated, can then be introduced through the secondary inlet system via pipe 6 or via the aperture 37 in insert 5. Such an arrangement may promote further mixing of gas and liquid.

Figures 6, 6A:
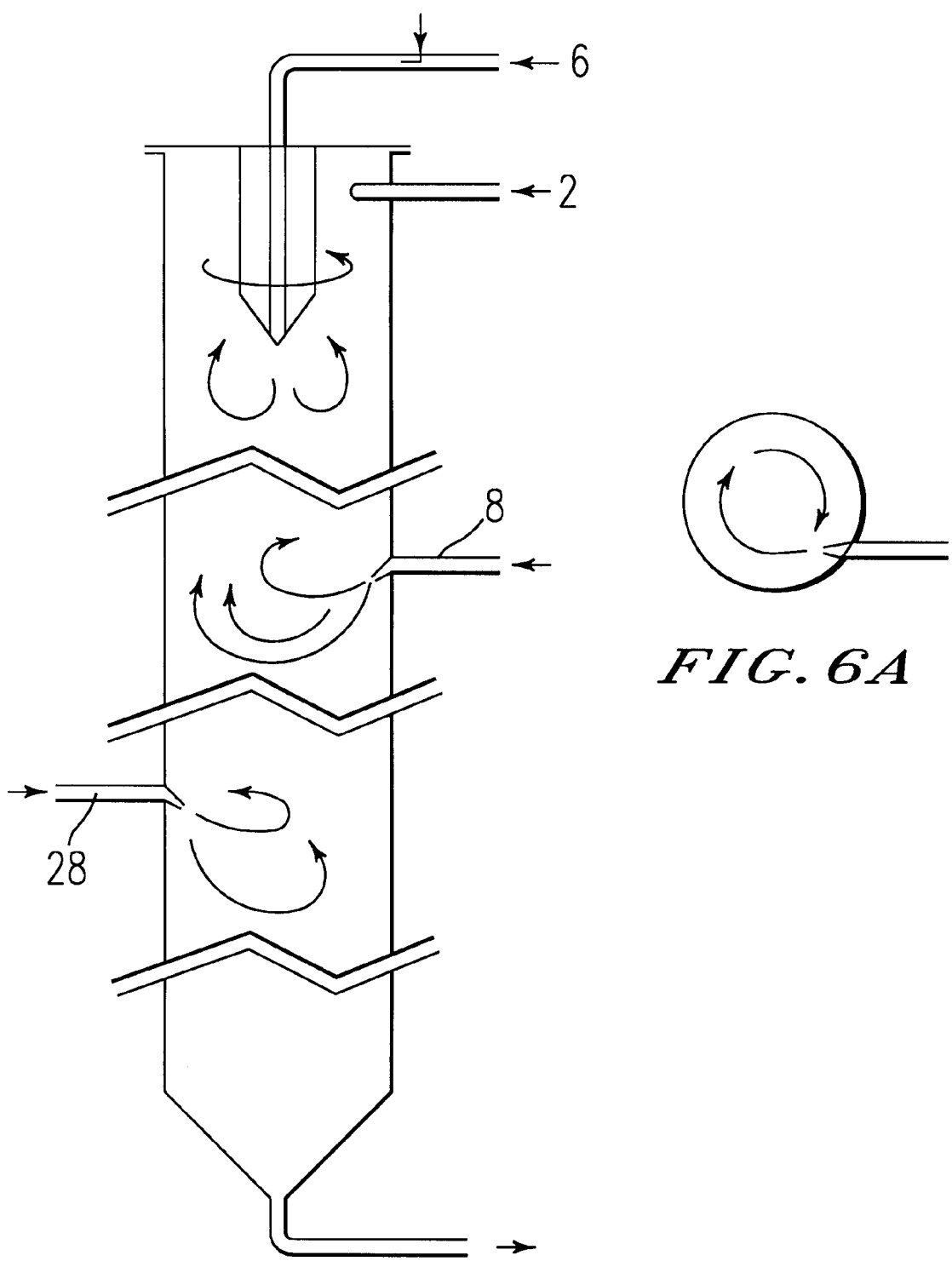
FIG. 6 shows a further embodiment in which a tertiary flow is introduced to flow countercurrently, as shown in FIG. 6A, and a fourth inlet is directed countercurrently thereto.

As can be seen from FIG. 6 and FIG. 6A, in which the primary input is via pipe 2, the secondary input in a longitudinal direction via input 6 and two further inputs are provided, a tertiary input 8 and a fourth input 28. In the embodiment shown, the tertiary input 8 is adapted to inlet fluid in a direction countercurrent to the general downflow flow of the reactor, while the fourth input 28 is adapted to allow input of fluid in a tangential direction which is kept current to that of the tertiary input but cocurrent with that of the primary input 2. In both cases, additional gas may be input through line 38.

Figure 4:
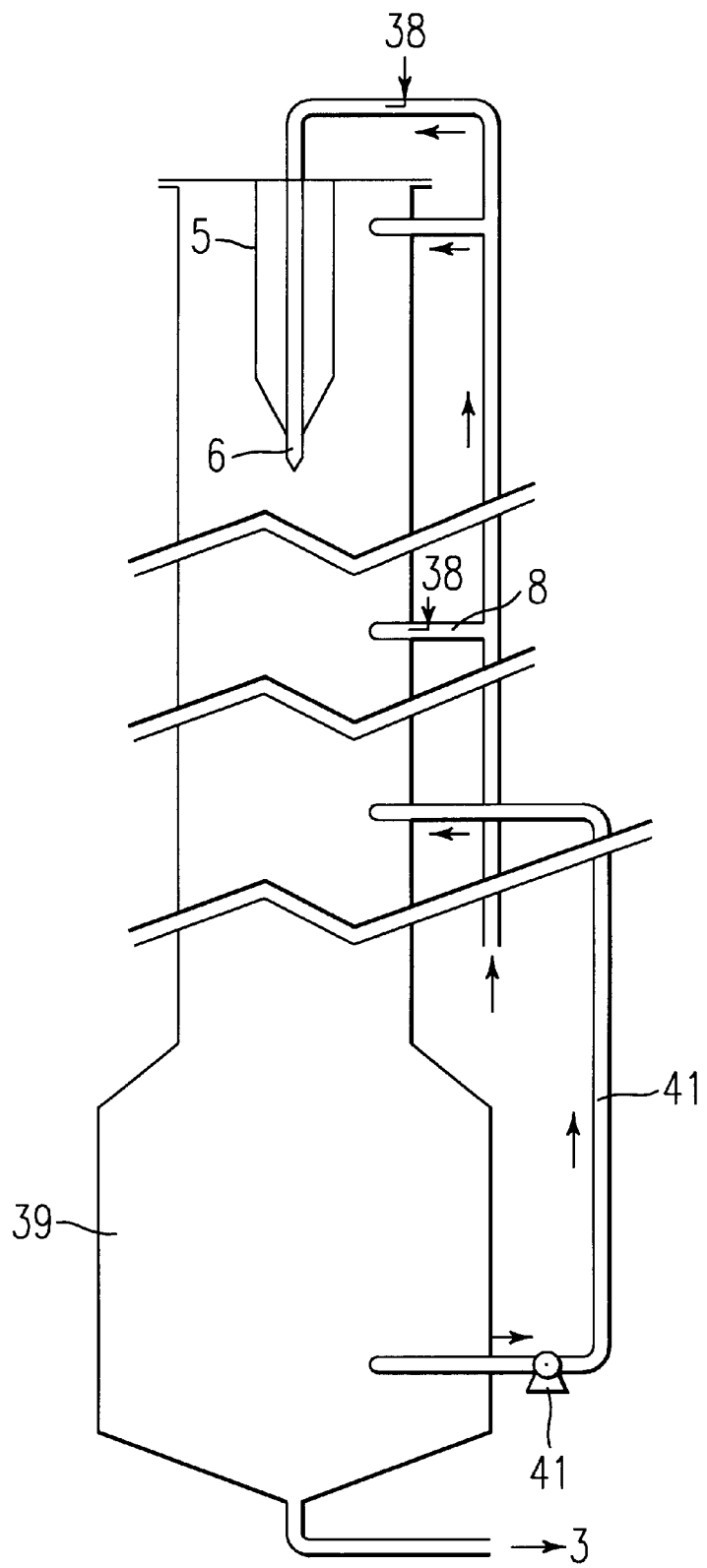
FIG. 4 shows schematically a variant of the embodiment shown in FIG. 3 with recirculated feed.
Figure 5:
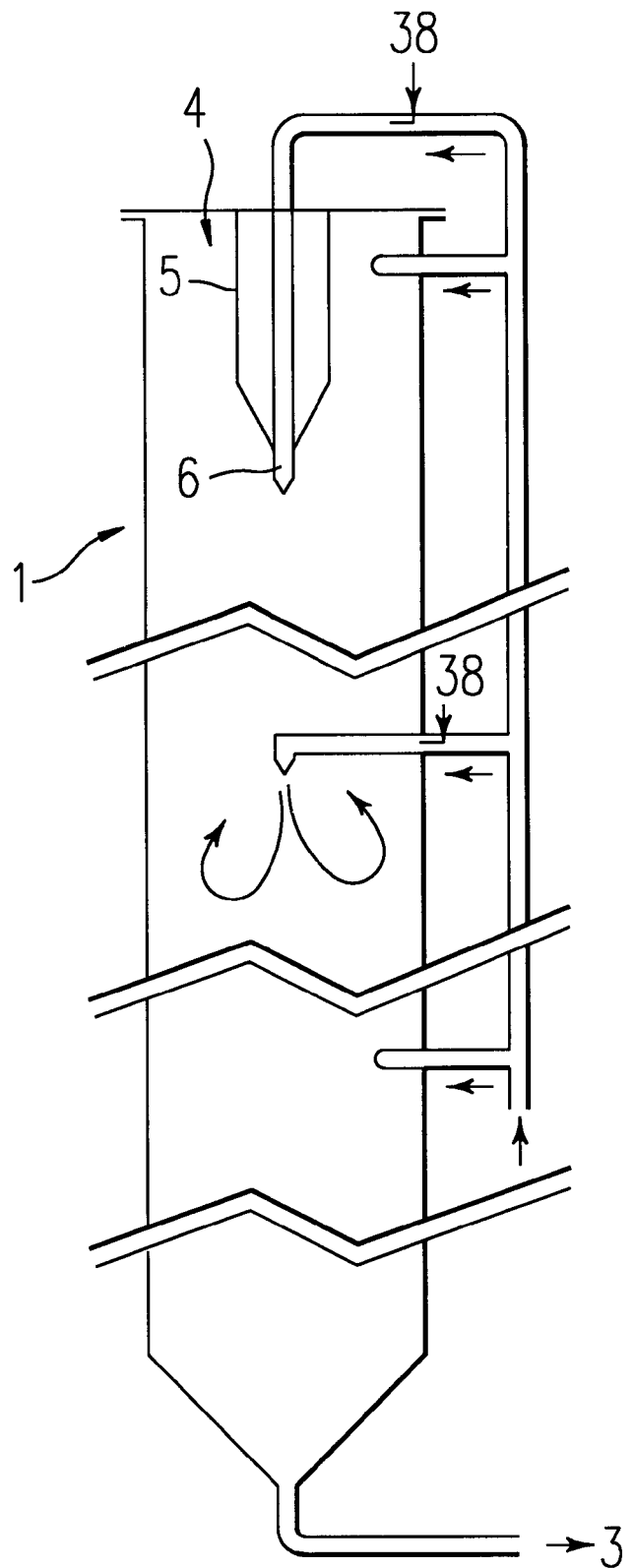
FIG. 5 shows a further embodiment of the invention in which a tertiary flow is introduced in a longitudinal direction.

Referring now to FIG. 4, there is shown a reactor in which a lowermost zone of the reactor, adjacent the outlet 3 is of increased diameter to form a settlement zone 39. Fluid from such a settlement zone 39 may be pumped back by means of pump 40 through pipe 41 and reintroduced to the column at any desired point thereof. FIG. 4 shows the reintroduction as a fourth stage inlet but other inlet positions are quite possible.

Figure 10:
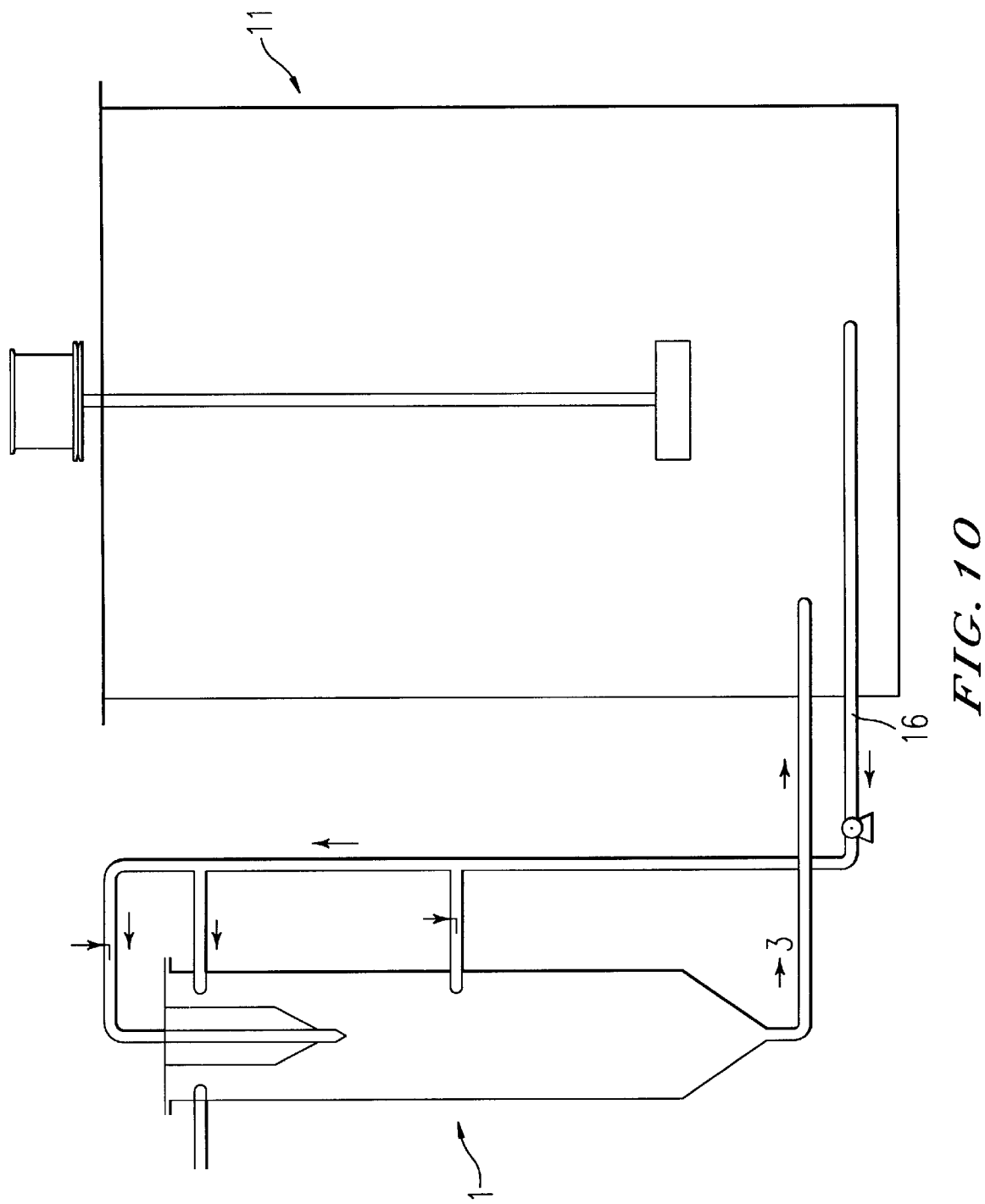
FIG. 10 shows a downflow contactor embodying the present invention in conjunction with a second stirred reactor in which fluid is recirculated from such second reactor to inlets of the primary reactor.

Referring now to FIG. 10, there is shown an apparatus for treatment of sewage sludge or other organic waste. The exit 3 of the reactor 1 leads to a second reactor in the form of a stirred tank 11 in which the waste has a longer residence time and which may have certain gas sparging bars which serve to gasify the liquid and maintain it in motion.

Liquid thus treated in the second reactor 11 is then recycled via pipe 16 to the primary inlet of the first reactor 1. Additional gas may be added to the inflow at point 38 and possibly other inlets. The recycled fluid may be split into two, one of which delivers the recycled liquid tangentially at a relatively high velocity, and the second of which delivers a greater quantity of recycled liquid, also tangentially, but into the rotational flow produced by the primary inlet.

Fresh liquid to be treated, optionally with the addition of gas, may be introduced into a lower part of the annulus, defined between the wall of the reactor and the insert extension 15.

In this embodiment, the settlement zone 39 of the reactor, adjacent the outlet 3, is of increased diameter to provide a settling zone. The organic material, in solution or aqueous suspension may be fed to a junction with an inlet pipe 38 for gas/oxygen or air which allows introduction of the gas into the liquid feed at or almost immediately upstream of a Venturi construction or orifice plate which serves to draw the gas into the liquid, begin the mixing dispersion process, and ensure that the mixture is ejected into the reactor 1 at the desired velocity. The Venturi or orifice plate may comprise part of a restricted inlet nozzle at the feed point to the column.

Figure 11:
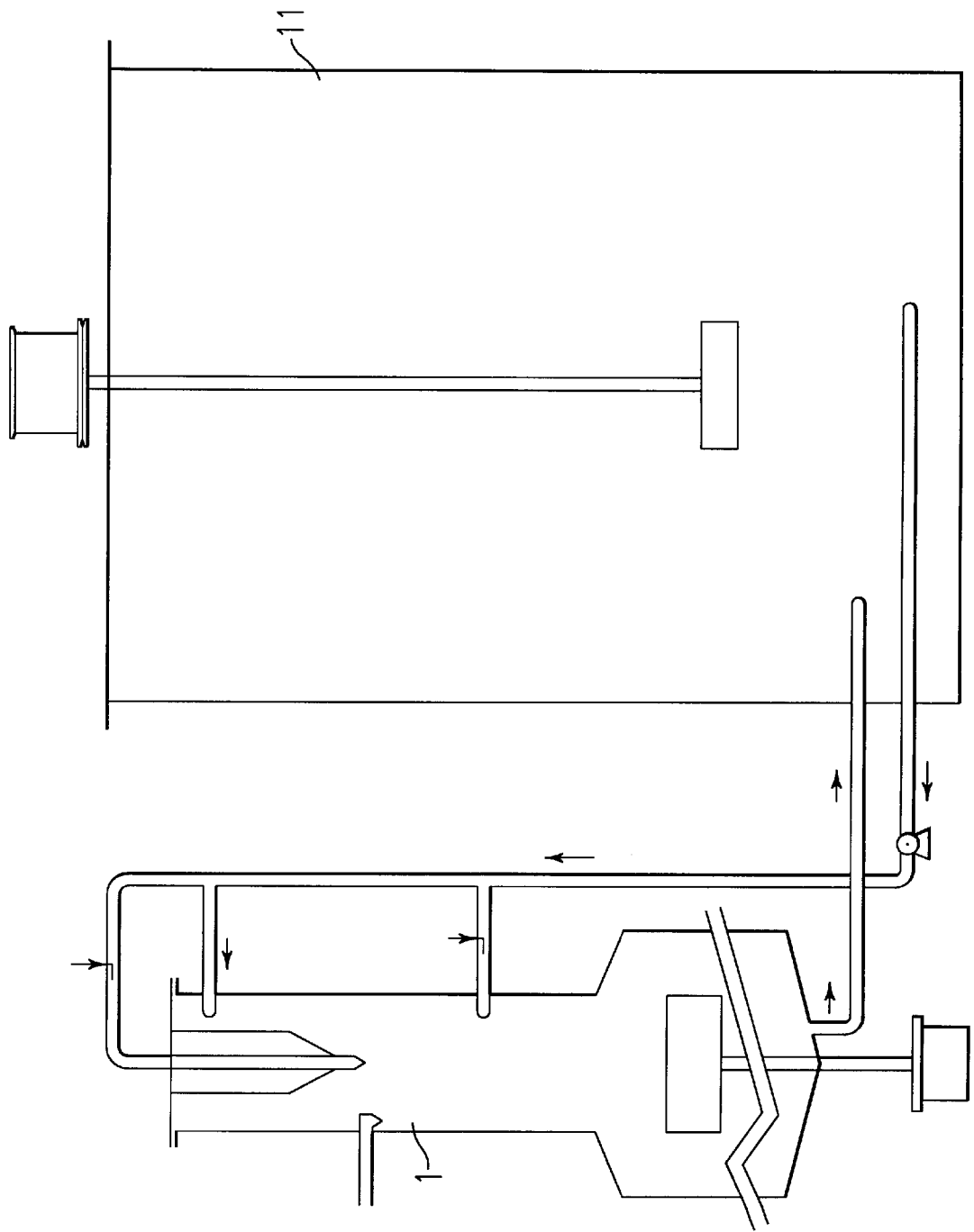
FIG. 11 shows a similar embodiment to that of FIG. 10 except that the primary reactor has a large diameter settlement zone at its base, in which there may be placed a stirrer mechanism.
Figure 12:
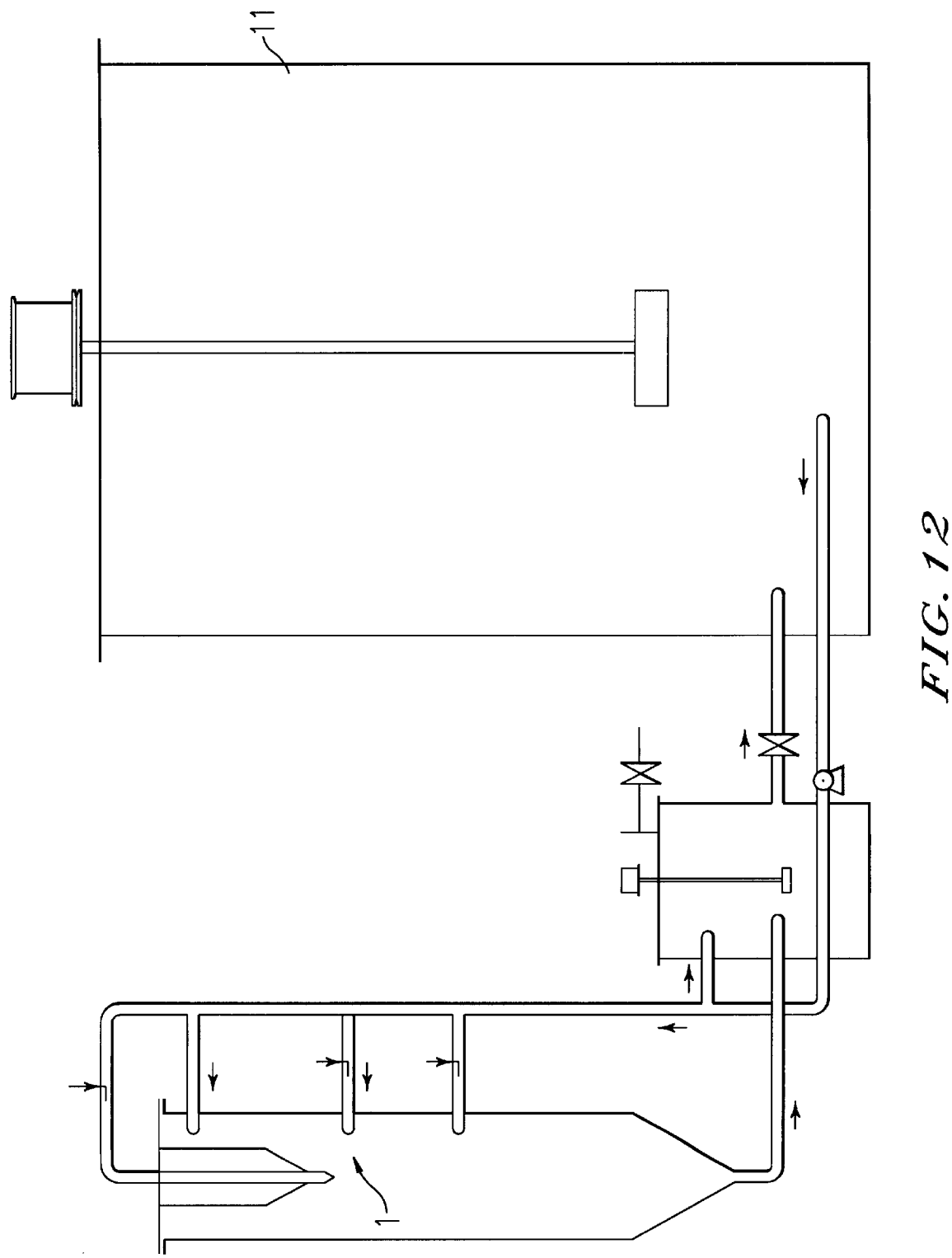
FIG. 12 shows a further embodiment of the invention in which the primary reactor is fed by recirculated fluid, with additional gas, from a secondary stirred reactor, which is itself fed from a tertiary reactor.

It is possible to combine two or more of such reactors in series, with the outlet 3 of a first reactor passing to at least one inlet of a second similar reactor. This is shown in FIGS. 10 to 12.

Additional oxygen or gas may be introduced at any point between the outlet 3 of the first reactor and the inlet of the second.

The outlet 3 of the second reactor may then pass to a fermenter which may take the form of a stirred tank 11. Liquid from the fermenter 11 may be pumped back to the first reactor's primary inlets 2 or thereto, via second inlets 6 or tertiary inlets 8. In every case, additional oxygen or air may be introduced to the liquid flow prior to the introduction through the secondary or tertiary inlets by means of gas inlets 38.

In a variant of the second inlet, there is a tertiary inlet 8, which is conformed partially to encircle an inlet extension 15, and thereby deliver its subsequent feed in a tangential direction, either co-currently or counter-currently.

Figures 7, 7A:
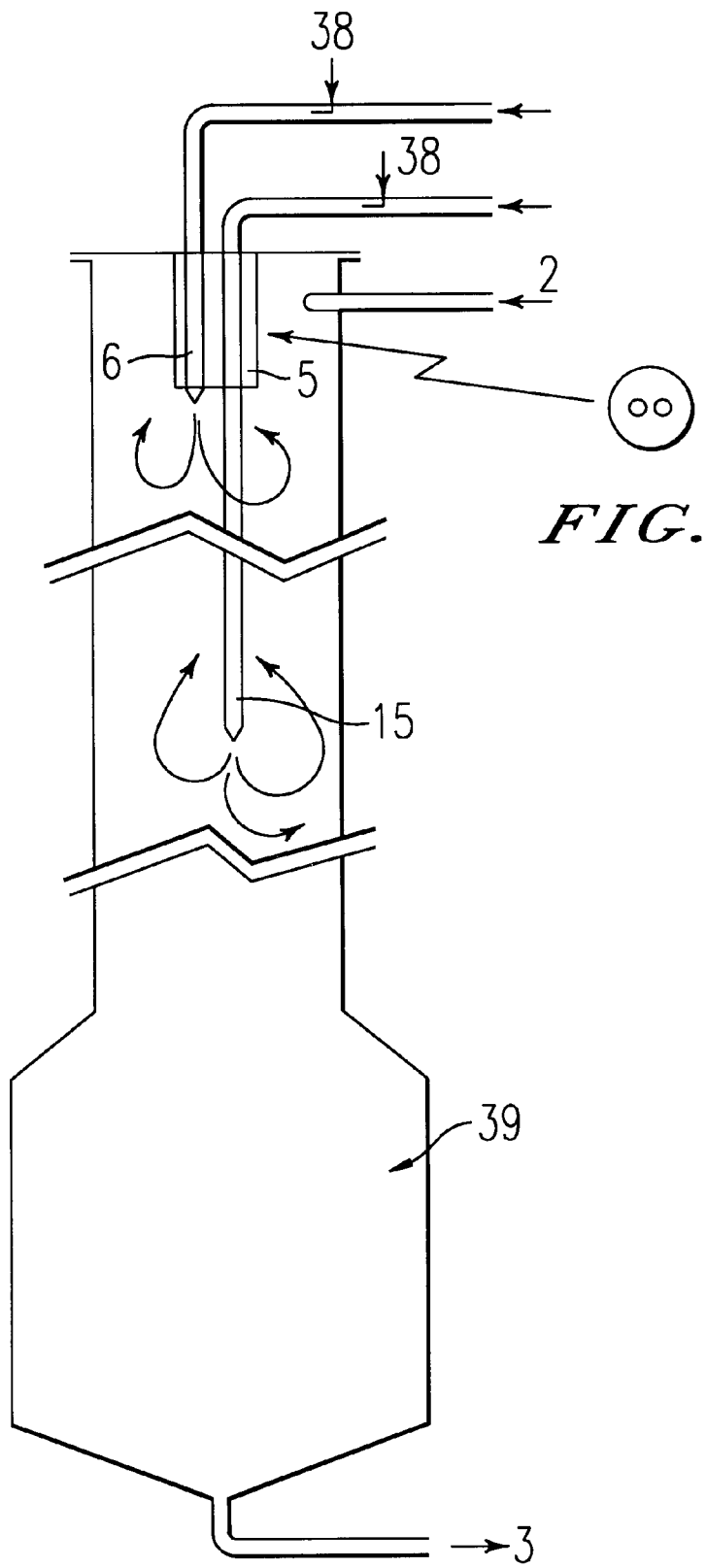
FIG. 7 is a further embodiment of the invention in which second and third inlets to the reactor are directed longitudinally while the primary inlet delivers a tangential flow.
FIG. 7A is a cross-section of the insert, which has two inlet pipes passing therethrough.

In FIG. 7 there is shown a reactor combining the features of many of the embodiments, including the stirrer, the insert extension 15, the plenum 39, a primary feed 2 (preferably from a recycling source), which passes through an ejector to entrain the gas vented in the plenum 39 and which therefore forms a tertiary inlet to the reactor at a lower point thereof A secondary inlet 6 in also provided in this embodiment. The outlet 3 may pass to a holding stirrer tank and be recycled therefrom as described above.

Figure 8:
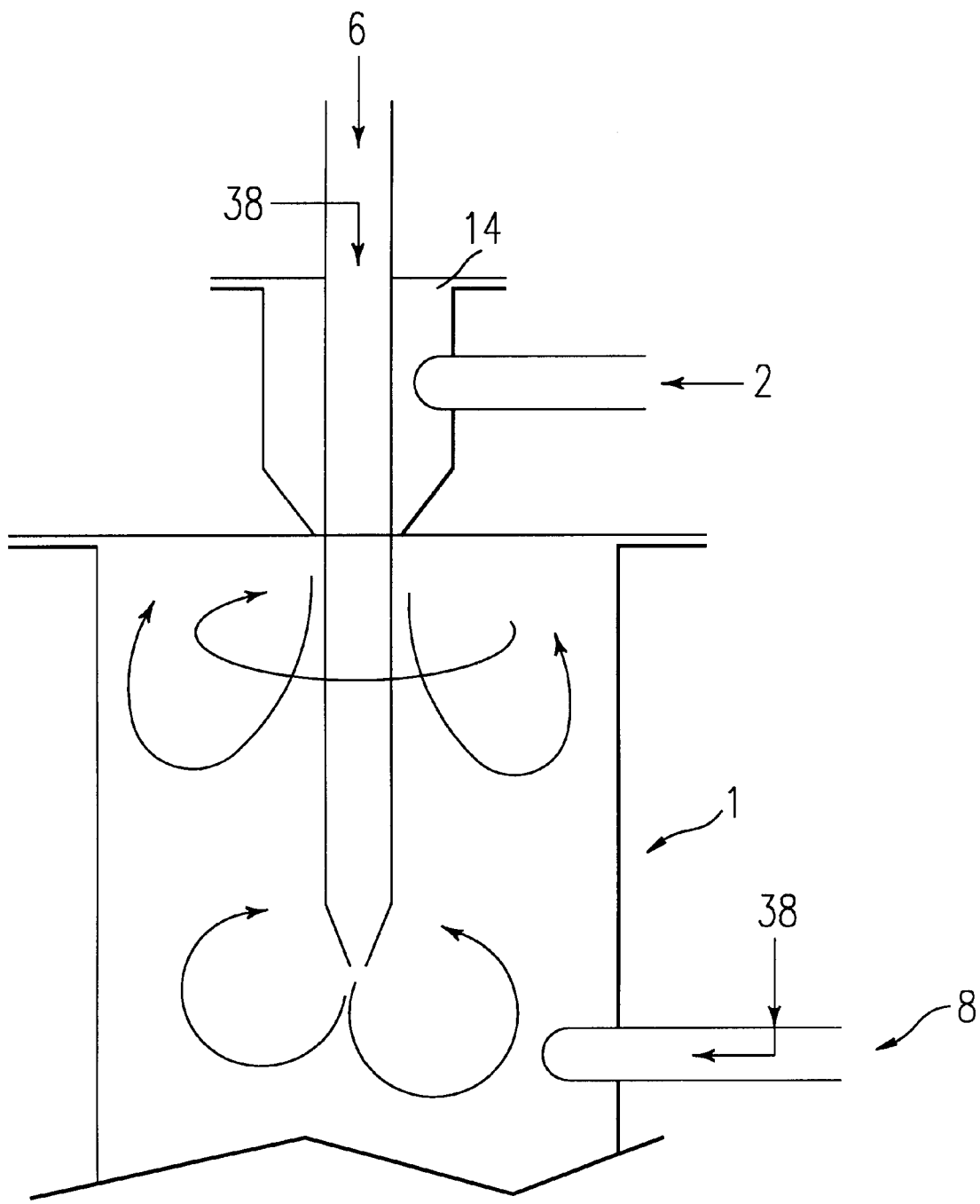
FIG. 8 shows a system in which the tangential primary input is separated from the main reactor body, but flows thereinto through an opening of restricted area.

A further embodiment is shown in FIG. 8, where instead of an annular space at the top of a substantially constant diameter reactor, there is provided an inlet zone 14 formed by a zone of the reactor which is of restricted external diameter. This serves a similar purpose to that conferred by the annulus of the preceding embodiments in that it is a zone of restricted cross sectional area in which more violent mixing between gas and liquid may take place. Secondary and/or tertiary inlets as shown as 6 and 8 may be provided in such an embodiment.

The above invention has been described by way of a vertical co-current downflow reactor. It is of course possible to use a horizontal or substantially horizontal reactor, in which case the reactor is substantially horizontal and an inlet feeds tangentially into a annulus formed between a wall and an insert 5. A stirrer may be provided at the downstream end of the reactor, given that there is a tendency for the gas/liquid mixture to separate as it passes horizontally along the reactor. The embodiment includes a collection zone 25 for such unentrained gas which is preferably recycled to the process via an ejector.

As may be seen, use of the present invention enables a bioreaction to be carried out in a comparatively small volume and on a substantially continuous basis with a high and rapid throughput. The present invention may of course be combined with other conventional processes in a multi stage treatment process. In such cases, recirculation of some or all of the fluids may be advisable.

The present invention is essentially, but not necessarily concerned with mixing gas and liquid in a confined area at one end of a reactor column. This call create a bubble zone at that end of the column which may be 3 to 4 feet in depth or length. This bubble zone in the confined volume promotes interreaction between the gas and liquid due to the large interfacial area between the liquid and gas, boosted by the tangential inlet flow.

Examples of the invention are now given

Mass Transfer Studies

Mass transfer studies were carried out using a design where the bubble dispersion could be extended down the full length of the column. As an indication of the degree of gas-liquid mass transfer, the volumetric gas-liquid mass transfer coefficient ($k_L a$) was calculated.

Two classical models were used to calculate $k_L a$, the plugflow model and the completely mixed (STR) model. These are shown in equations 1 and 2 below.

Plugflow Model $$k_L a = \frac{Q}{V_R} \ln \frac{(C^* - C_i)}{(C^* - C_f)} \quad (1)$$

Completely Mixed Model $$k_L a = \frac{Q}{V_R} \frac{(C_f - C_i)}{(C^* - C_f)} \quad (2)$$

Where $K_1 a$ = Volumetric gas liquid mass transfer coefficients ($s'^{-1}$).

$Q$ = Volumetric flowrate through the reactor ($m^3 s^{-1}$), $V$ = Reactor volume ($m^3$), $C^*$ = Equilibrium concentration of gas dissolved in liquid (mol/l), $Ci$ = Initial concentration of gas dissolved in liquid(mol/l), $Cf$ = Concentration of gas dissolved in liquid leaving the reactor (mol/l)

The reactor was operated on a once through basis and the following operating conditions were used for all runs;

Reaction temperature 10.8–12.5° C.

Reaction pressure 13.0–24.0 psig

Column flowrate 3.0–20.0 l/min

Top swirl flowrate 6.0–17.0 l/min

Gas holdup 35–50%

As a comparison, a conventional CDC reactor was set up and the gas-liquid mass transfer coefficients were calculated for the CDC and compared.

The results are shown below.

| Reactor configuration | $k_L a\ s^{-1}$ (Plugflow) | $k_L a\ s^{-1}$ (STR) |
|---|---|---|
| Medium insert (3 mm swirl inlet diam) | 0.22–0.63 | 0.33–1.57 |
| Medium insert (4 mm swirl inlet diam) | 0.33–0.65 | 0.76–2.45 |
| Wide insert (4 mm swirl inlet diam) | 0.28–0.63 | 0.21–1.91 |
| Normal CDC (3 mm orifice) | 0.12–0.35 | 0.15–0.61 |

Very large values of $k_L a$ were calculated using both models indicating the good gas-liquid contacting and effective gas-liquid mass transfer achieved in the reactor.

Generally, when the wide insert reactor inlet was used (higher swirl circulation velocity achieved), on overall average slightly larger values of $k_L a$ were determined when compared with the values calculated using the medium sized insert reactor inlet. Both sized reactor inlets of the design gave better values of $k_L a$ than the conventional CDC, indicating better gas-liquid mass transfer was achieved in the reactor than the CDC reactor for oxygen/water absorbtion.

It should also be noted that it was difficult for the dispersion to collapse and for gas pockets to be formed. However, if a gas pocket was formed it was very easy to regain the stable bubble dispersion by increasing either the longitudinal liquid flowrate or the tangential flowrate.

In an attempt further to enhance the mass transfer capabilities of the reactor, swirlflow at a lower point of the reactor was incorporated into the reactor system, via a 3 mm tangential inlet. The jet created through the tangential inlet would allow a greater degree of bubble shear and turbulence in the lower region of the column and hence increase the degree of gas-liquid mass transfer further down the column. Due to limitations of the reactor system pump, swirl flowrates at the bottom of the reactor were varied from 2–4 l/min.

The following range of $k_L a$ values were calculated for swirlflow operation;

| Reactor configuration | $k_L a\ s^{-1}$ (Plugflow) | $k_L a\ s^{-1}$ (STR) |
|---|---|---|
| Swirlflow (wide insert) | 0.50–0.57 | 1.15–1.52 |
| Swirlflow (medium insert) | 0.26–0.36 | 0.50–0.83 |

Again large values of $k_L a$ were determined using both STR and plugflow models indicating good gas-liquid mixing and effective gas-liquid mass transfer. As well as giving high values of $k_L a$, swirlflow in the lower region of the column also has the added advantage of holding the gas in the reactor and enabling 100% gas utilisation, even at high column flowrates.

As in the case of the previous studies it can be seen that when using the wide insert reactor inlet slightly better values of $k_L a$ were obtained.

Examples are given as shown in FIGS. 13 and 14.

Because of the comparatively high inlet velocity into a restricted area, there is increased mixing of the components, greater turbulence, and thereby a higher rate of solution of oxygen/air/gas in the liquid. As the bubble mixture moves downwardly or outwardly from the inlet zone, its rate of downflow is greater than the downflow rate at a median zone of the column. This restricts the rate of rise of bubbles in the constricted area inlet section and thereby obviates any continuing accumulation of gas at the top or inlet end of the column.

In order to control the bubble development in the mixture, it has been found that, in some cases, it may be advantageous to introduce liquid only at the primary inlet 2 and to introduce gas or gas and liquid at the secondary inlet 6. Further gas and/or liquid can be introduced at tertiary and further inlets 8.

In the absence of the confined area inlet zone of the present invention, it could be expected that the downflow velocity of the liquid or liquid/gas would be of the order of 10 cm/sec. However, one advantage of the present invention is that due to the restricted area at the top of the column, the downflow velocity may be at least twice that figure. Since it is thought that 3 to 5 mm bubbles in water will rise at a rate of 20 cm/sec, it is very unlikely that such bubbles will rise into or through the restricted area of the inlet zone. Larger bubbles in water may rise at a slightly greater rate, such as 20 to 30 cm/sec, but one advantage of the invention is that the formation of larger bubbles is discouraged by the velocity of introduction of fluid mixture, and possibly also the presence of column wall surface effects. The viscosity of the mixture will of course be increased by any presence therein of solid material, and by the rate of rotational circulation of the inlet fluid flow.

The high speed of fluid circulation in the restricted area inlet zone, together with the provision of a roughened surface, would be expected to re-disperse any larger bubbles, say of size greater than 5.0 mm. Hence, there will, as described above, be less tendency for the gas to rise through the column.

In systems where larger bubbles may be expected, it may be advantageous to feed a secondary stream of liquid only into the initial confined space of the inlet zone and to feed the gas/liquid mixture into the confined space at a lower or downstream point thereof.

In some embodiments of the invention, there is provided a lower or downstream end of the column which has a larger diameter and therefore volume. It or the presence in that space of a stirrer may cause small downflowing bubbles, say of 1 mm diameter, to coalesce in which case such larger coalesced bubbles, which as stated above, are more likely to rise, will in fact rise and react with further liquid input at a median point of the reactor.

The extended part 15 of the insert obviates any tendency to vortex formation throughout the bubble form structure, which may have a depth of between 3 and 4 feet. Furthermore, such an insert may add to the turbulence and mixing in the center of the column. This latter effect may be further increased by providing the insert with a roughened surface. Thus, the presence of the insert extension 15 will fill any void which might be caused by the circulatory flow of fluid and will permit a higher rate of circulation in the column.

If higher gas solubility is required, the present invention may be operated at a pressure greater than atmospheric pressure. The energy requirements of the process are lower than those of conventional apparatus of the type having one or more larger holding reactors with gas sparging. This is due to the ability to carry out the process in a shorter overall reaction time and the need for less vigorous stirring in the holding reactors.

As has been described, there is a quite distinct difference in the flow patterns between the reactor of the present invention and those described in UK Patent No. 1596738 and U.S. Pat. No. 4,843,343. In the present application, the downflowing jet stream of dispersed gas as small bubbles is surrounded by a downflowing stream of comparatively low oxygen content. However, in the above two patents, the downflowing jet stream of dispersed gas is surrounded by a recirculation stream from lower in the column which has a high oxygen concentration. Hence, in the present invention the oxygen concentration gradient from the jet to the surrounding liquid is greater than in the previous patents, thus aiding mass transfer, particularly at the top of the column where the overall oxygen concentration level is lower. In the apparatus embodying the invention, the rotation of downflowing low oxygen stream surrounding the jet stream adds to the stability of the column.

What is claimed is:

1. A method of contacting a gas and a liquid which comprises providing an elongate substantially cylindrical reactor column having an inlet region of reduced cross sectional area adjacent a first end thereof; introducing a first flow comprising at least some of the liquid into said inlet region in a direction substantially tangential to the longitudinal axis of the reactor column to cause rotational flow of the first flow within said inlet region and at such a high velocity as to re-disperse any large bubbles of gas that might accumulate in the inlet region; introducing a second flow comprising a gas stream through a second inlet disposed at an intermediate region of said reactor column adjacent an end of the inlet region.

2. A method as claimed in claim 1, wherein the second flow is introduced at a point where the rotational first flow in the reactor column would cause a central vortex region to form, said second flow being directed generally longitudinally of the reactor column.

3. A method as claimed in claim 1, wherein the second flow is introduced at a point where the rotational first flow in the reactor column would cause a central vortex region to form, said second flow being directed in a rotational sense co-current with respect to the first flow.

4. A method as claimed in claim 1, wherein the second flow is introduced at a point where the rotational first flow in the reactor column would cause a central vortex region to form, said second flow being directed in a rotational sense counter current with respect to the first flow.

5. A method as claimed in claim 1, wherein the first flow comprises gas and liquid combined initially upstream of the reactor column inlet region at constriction means.

6. A method as claimed in claim 5, wherein the velocity of flow of the gas/liquid at the constriction is greater than 150 cms/sec.

7. A method as claimed in claim 1, wherein the second flow introduced through the second inlet is so heated as to raise the overall temperature of the liquid within the reactor column.

8. A method as claimed in claim 1, comprising introducing additional flow by means of a third inlet at an intermediate region of said reactor column.

9. A method as claimed in claim 8, wherein said third flow is directed tangentially to the longitudinal axis of the reactor column.

10. A method as claimed in claim 1, wherein the liquid is organic waste.

11. A method as claimed in claim 10, wherein the liquid is sewage sludge.

12. A method of carrying out a bio-reaction involving gas liquid contact which comprises providing an elongate substantially cylindrical first reactor column having an inlet region of reduced cross sectional area adjacent a first end thereof and an outlet at an opposite end thereof; introducing a first flow comprising at least some of the liquid into said inlet region in a direction substantially tangential to the longitudinal axis of the reactor column to cause rotational flow of the first flow within said inlet region and at such a high velocity as to re-disperse any large bubbles of gas that might accumulate in the inlet region; introducing a second flow comprising a gas stream through a second inlet disposed at an intermediate region of said region of said reactor column adjacent an end of the inlet region; providing a second reactor; and passing gas/liquid from said outlet to an inlet of said second reactor.

13. A method as claimed in claim 12, comprising removing liquid from an outlet of said second reactor and directing said liquid to become at least part of said first flow.

14. A method as claimed in claim 12, comprising removing liquid from an outlet of said second reactor, mixing said liquid with a gas, and directing said mixture to become at least a part of said second flow.

15. A method as claimed in claim 12, wherein said gas contains oxygen.

16. An apparatus for contacting gas and liquid comprising: an elongate reactor column; first inlet means adjacent a first end thereof, outlet means adjacent a second end thereof and second inlet means intermediate said first and second ends, the first inlet means being so disposed as to direct incoming liquid tangentially to the longitudinal axis of the reactor column and into an inlet zone having a smaller cross sectional area than that of the major part of the reactor column; said second inlet means being disposed to deliver gas to a point adjacent to a longitudinally downstream end of the inlet zone of the reactor column.

17. An apparatus as claimed in claim 16, wherein the inlet zone comprises an annulus adjacent the first end of the reactor column, said annulus having an outer diameter substantially equal to that of the reactor column, and an inner diameter formed by an insert.

18. An apparatus as claimed in claim 17, wherein said insert is substantially cylindrical.

19. An apparatus as claimed in claim 17, wherein said insert is substantially conical.

20. An apparatus as claimed in claim 17, wherein said insert is substantially frustoconical.

21. An apparatus as claimed in claim 17, wherein the insert has a surface provided with protrusions to promote increased turbulence.

22. An apparatus as claimed in claim 17, wherein said second inlet means is located adjacent to a longitudinally downstream portion of the annulus.

23. An apparatus as claimed in claim 22, wherein the second inlet means comprises a pipe extending longitudinally into the reactor column and passing through the insert.

24. An apparatus as claimed in claim 22, wherein the second inlet means comprises an aperture at a downstream end of the insert communicating with an inlet to the interior of the insert.

25. An apparatus as claimed in claim 16, wherein an additional inlet means is provided further downstream of the inlet zone and is adapted to introduce further fluid to a median zone of the reactor column.

26. An apparatus for carrying out a bio-reaction involving a gas and a liquid, as hereinbefore defined, the apparatus comprising; a first reactor column vessel having an inlet zone at one end thereof of reduced cross sectional area compared to the general diameter of the first reactor column; first inlet means into said inlet zone to introduce the gas/liquid mixture in a tangential direction with respect to the longitudinal axis of the reactor column; outlet means at an opposite end of the reactor column; a second reactor vessel having an inlet means connected to the outlet means of said first reactor column; stirring means therein; and outlet means therefrom.

27. An apparatus as claimed in claim 26, wherein liquid from the outlet of said second reactor is recirculated to said first inlet means of said first reactor column.

28. An apparatus as claimed in claim 27, wherein there are provided means to introduce additional gas to such recirculated liquid.

29. An apparatus for carrying out a bio-reaction involving gas and liquid, comprising: an elongate first reactor column; first inlet means adjacent a first end thereof; outlet means adjacent a second end thereof; a second inlet means intermediate said first and second ends; and a second reactor having an inlet means connected to the outlet means of said first reactor column; the first inlet means being so disposed as to direct incoming liquid tangentially to the longitudinal axis of the reactor column and into an inlet zone having a smaller cross sectional area than that of the major part of the reactor column; said second inlet means being disposed to deliver gas to a point adjacent a longitudinally downstream end of the inlet zone of the reactor column.

30. An apparatus as claimed in claim 29, wherein an outlet of said second reactor is connected to said first inlet means.

31. An apparatus as claimed in claim 29, wherein an outlet of said second reactor is connected to said second inlet means, and means are provided to introduce gas into liquid recirculated from said second to said first reactor column.

32. An apparatus for contacting gas and liquid comprising:
    an elongate reactor column;
    a first inlet adjacent a first end thereof;
    an outlet adjacent a second end thereof and a second inlet intermediate said first and second ends;
    the first inlet being so disposed as to direct incoming liquid tangentially to the longitudinal axis of the reactor column and into an inlet zone having a smaller cross sectional area than that of the major part of the reactor column;
    said second inlet being disposed to deliver gas to a point adjacent to a longitudinally downstream end of the inlet zone of the reactor column.

33. An apparatus as claimed in claim 32, wherein the inlet zone comprises an annulus adjacent the first end of the reactor column, said annulus having an outer diameter substantially equal to that of the reactor column, and an inner diameter formed by an insert.

34. An apparatus as claimed in claim 33, wherein said insert is substantially cylindrical.

35. An apparatus as claimed in claim 33, wherein said insert is substantially conical.

36. An apparatus as claimed in claim 33, wherein said insert is substantially frustoconical.

37. An apparatus as claimed in claim 33, wherein the insert has a surface provided with protrusions to promote increased turbulence.

38. An apparatus as claimed in claim 33, wherein said second inlet means is located adjacent to a longitudinally downstream portion of the annulus.

39. An apparatus as claimed in claim 38, wherein the second inlet means comprises a pipe extending longitudinally into the reactor column and passing through the insert.

40. An apparatus as claimed in claim 38, wherein the second inlet means comprises an aperture at a downstream end of the insert communicating with an inlet to the interior of the insert.

41. An apparatus as claimed in claim 32, wherein an additional inlet means is provided further downstream of the inlet zone and is adapted to introduce further fluid to a median zone of the reactor column.

42. An apparatus for carrying out a bio-reaction involving a gas and a liquid, the apparatus comprising;
    a first reactor column having an inlet zone at one end thereof of reduced cross sectional area compared to the general diameter of the first reactor column;
    a first inlet into said inlet zone to introduce the gas/liquid mixture in a tangential direction with respect to the longitudinal axis of the reactor column; and
    an outlet at an opposite end of the reactor column;
    a second reactor vessel having an inlet connected to the outlet of said first reactor column; a stirring mechanism located therein and an outlet provided therefrom.

43. An apparatus as claimed in claim 26, wherein liquid from the outlet of said second reactor is recirculated to said first inlet of said first reactor column.

44. An apparatus as claimed in claim 27, wherein there are provided a mechanism for introducing additional gas to such recirculated liquid.

45. An apparatus for carrying out a bio-reaction involving gas and liquid, comprising:

an elongate first reactor column;

a first inlet adjacent a first end thereof;

an outlet adjacent a second end thereof;

a second inlet intermediate said first and second ends;

a second reactor having an inlet connected to the outlet of said first reactor column;

the first inlet being so disposed as to direct incoming liquid tangentially to the longitudinal axis of the reactor column and into an inlet zone having a smaller cross sectional area than that of the major part of the reactor column; and said second inlet being disposed to deliver gas to a point adjacent a longitudinally downstream end of the inlet zone of the reactor column.

46. An apparatus as claimed in claim 45, wherein an outlet of said second reactor is connected to said first inlet.

47. An apparatus as claimed in claim 45, wherein an outlet of said second reactor is connected to said second inlet, and a mechanism is provided for introducing gas into liquid recirculated from said second reactor to said first reactor column.

* * * * *